(12) United States Patent
Umeno

(10) Patent No.: US 7,901,463 B2
(45) Date of Patent: Mar. 8, 2011

(54) HAIR COLOR

(75) Inventor: Takashi Umeno, Fujioka (JP)

(73) Assignee: Mitsubishi Pencil Co., Ltd., Shinagawa-Ku, Tokyo (JP)

( * ) Notice: Subject to any disclaimer, the term of this patent is extended or adjusted under 35 U.S.C. 154(b) by 0 days.

(21) Appl. No.: 10/545,202

(22) PCT Filed: Feb. 16, 2004

(86) PCT No.: PCT/JP2004/001628
§ 371 (c)(1),
(2), (4) Date: Aug. 11, 2005

(87) PCT Pub. No.: WO2004/073667
PCT Pub. Date: Feb. 9, 2004

(65) Prior Publication Data
US 2006/0137109 A1 Jun. 29, 2006

(30) Foreign Application Priority Data

Feb. 21, 2003 (JP) ................. 2003-043703

(51) Int. Cl.
*A61Q 5/10* (2006.01)
(52) U.S. Cl. ............. 8/405; 8/406; 8/435; 8/552; 8/581; 8/632
(58) Field of Classification Search .............. 8/405, 406, 8/435, 552, 581, 632
See application file for complete search history.

(56) References Cited

U.S. PATENT DOCUMENTS 6,905,521 B2 * 6/2005 Tsuchiya ................. 8/405
2003/0066142 A1 4/2003 Tsuchiya

FOREIGN PATENT DOCUMENTS

| EP | 0 533 937 A1 | 3/1991 |
| EP | 1238648 A1 | 9/2002 |
| JP | 5-105615 A | 4/1993 |
| JP | 9-110632 A | 4/1997 |
| JP | 9-255540 A | 9/1997 |
| JP | 10-29919 A | 2/1998 |
| JP | 10-273431 A | 10/1998 |
| JP | 11-124319 A | 5/1999 |
| JP | 11124319 A * | 5/1999 |
| JP | 2001-130187 A | 5/2001 |
| JP | 2001-172141 A | 6/2001 |
| JP | 2001-278754 A | 10/2001 |
| JP | 2002-104942 A | 4/2002 |
| WO | WO 99/13843 A1 | 3/1999 |

OTHER PUBLICATIONS

STIC Search Report dated May 25, 2007.*
English Abstract of the Japanese Patent No. JP 11124319 A.*
* cited by examiner

*Primary Examiner* — Eisa B Elhilo
(74) *Attorney, Agent, or Firm* — Buchanan Ingersoll & Rooney PC

(57) ABSTRACT

In order to provide an accumulatively dying hair color of a hair manicure type which does not require washing of hair immediately after used and by which hair are gradually dyed by repeating use thereof as a temporary coloring material, used is a hair color comprising 0.1 to 3% by weight of at least one of water-soluble dyes, 1.5 to 10% by weight of a nonionic or anionic silicone base resin, 0.1 to 1.5% by weight of an amphoteric acryl resin, 3 to 20% by weight of a hair dying auxiliary, 30 to 80% by weight of a lower alcohol and 5 to 50% by weight of water and having a pH controlled to 2 to 5.

4 Claims, 3 Drawing Sheets

HAIR COLOR

TECHNICAL FIELD

The present invention relates to an accumulatively dying hair color of a hair manicure type which does not require washing of hair immediately after used and by which the hair is gradually dyed by repeating use thereof as a temporary coloring material.

BACKGROUND ART

Permanent hair colors (oxidative hair colors) and semi-permanent hair colors (acidic hair colors) which have so far usually been used have such great defects that dying operation in use is complicated and troublesome and that the surroundings, cloths and persons applied are dyed.

Accordingly, they have to be applied usually in beauty solons or they have to be applied by ourselves in bathing so that they can be washed away soon even if stained, and therefore an excessive burden has been imposed on the users.

An accumulatively dying temporary hair color which comprises 0.01 to 3% by weight of an acidic dye as a coloring agent, 1.5 to 10% by weight of a nonionic or anionic silicone base resin, 3 to 20% by weight of a hair dying auxiliary, 30 to 80% by weight of a lower alcohol and 5 to 50% by weight of water and which has a pH of 2 to 5 and a viscosity of 100 mPa·s or less is disclosed in, for example, Japanese Patent Application Laid-Open No. 172141/2001 filed by the present applicant as a hair manicure which can reduce the above burdens and which can accumulatively dye hair by simply repeating use even if dying per once is little. Further, an acidic hair color composition comprising 0.01 to 1% of at least one of acidic dyes, 0.1 to 10% of an acid as a pH controller, 1 to 20% of an aromatic alcohol as a penetrating agent, 1 to 20% of a lower alcohol as a solvent and 0.01 to 5% of a high molecular compound such as xanthan gum as a thickener is disclosed in Japanese Patent Application Laid-Open No. 104942/2002.

The hair color disclosed in the former gazette described above is excellent as a hair color which can accumulatively dye hair, but an initial viscosity of the content liquid can not help coming up to 10 to 20 mPa·s in order to obtain satisfactory water resistance, and therefore the content liquid has to be introduced up to an applying part by clicking operation when the applicator is filled with this hair color. In addition thereto, because of a high viscosity, it takes time until the content liquid penetrates into the applying part, and it is difficult to control a liquid amount to be held in the applying part, so that it is a matter of concern that cloths, skins and furniture are stained by liquid blobbing caused with excessive clicking operation by a user. Further, a trial use shows that this applicator has some such problems that it takes time until the liquid oozes out after carrying out clicking operation because of a high viscosity of the content liquid, so that the users have such first impression in a certain case that dying is inferior.

Further, it is disclosed that the water resistance is improved by the high molecular compound such as xanthan gum in the acidic hair color disclosed in the latter gazette described above. However, it has problems in that only about 20% of a lower alcohol can be blended and that a dye can be blended only to a concentration of maximum 0.5% because of insufficient ability in water resistance of xanthan gum, so that dying is inferior. Further, since a use method thereof is not positively taught, conventional complicated dying operation remains as it is, and the usability can not be expected to be improved, so that less merits are provided to the users.

In light of the problems described above on the prior art, the present invention intends to solve them, and an object thereof is to provide a hair color excellent in an accumulative dying property, water resistance and usability and suited to an applicator of a sliver type for hair in which the hair color can ooze out to an applying part without allowing the users to carry out specific operations by reducing a viscosity of a hair color composition.

DISCLOSURE OF THE INVENTION

Intensive investigations repeated by the present inventors on the problems of the prior art described above have resulted in finding that a hair color meeting the object described above can be obtained by adding a specific amount of a specific component to a system containing a water-soluble dye, a nonionic or anionic silicone base resin, a hair dying auxiliary, a lower alcohol and water, and thus the present invention has come to be completed.

That is, the present invention comprises the following items (1) to (5).

(1) A hair color comprising 0.1 to 3% by weight of at least one of water-soluble dyes, 1.5 to 10% by weight of a nonionic or anionic silicone base resin, 0.01 to 1.5% by weight of an amphoteric acryl resin, 3 to 20% by weight of a hair dying auxiliary, 30 to 80% by weight of a lower alcohol and 5 to 50% by weight of water and having a pH controlled to 2 to 5.

(2) The hair color as described in the above item (1), wherein the water-soluble dye is an acidic dye.

(3) The hair color as described in the above item (1) or (2), wherein the nonionic or anionic silicone base resin is a block copolymer of polydimethylsiloxane and methacrylic acid and/or a methacrylic acid ester.

(4) The hair color as described in any of the above items (1) to (3), wherein the amphoteric acryl resin is an N-methacryloyloxyethyl-N,N-dimethylammonium-α-N-methylcarboxybetaine.methacrylic acid alkyl ester copolymer represented by the following Formula (I):

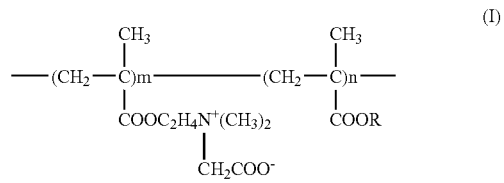

wherein R is an alkyl group having 1 to 18 carbon atoms, and an average molecular weight of the copolymer is 80,000 to 220,000.

(5) The hair color as described in any of the above items (1) to (4), wherein the hair color has a viscosity of 8 mPa·s or less.

BRIEF DESCRIPTIONS OF THE DRAWINGS

BEST MODE FOR CARRYING OUT THE INVENTION

Figure 1:
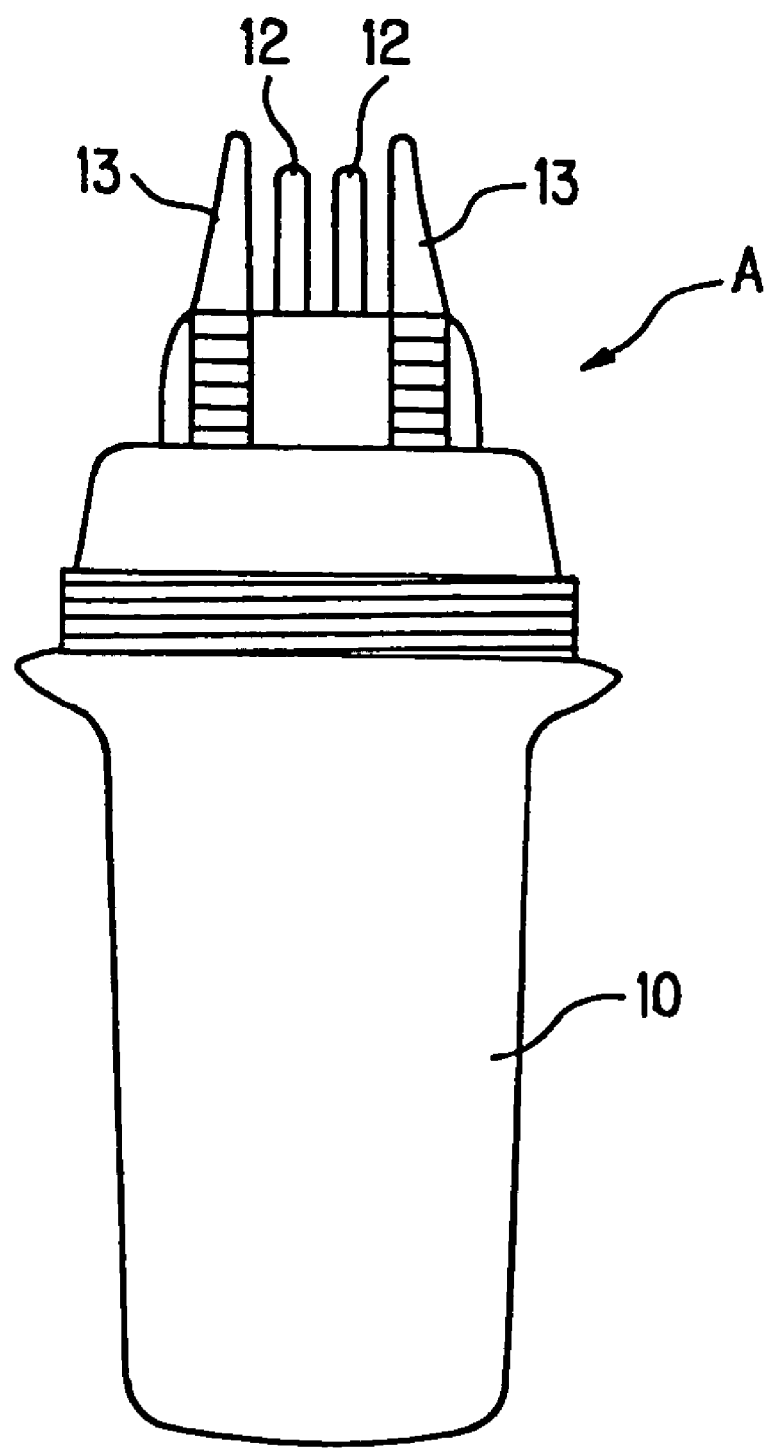
FIG. 1 is a side view showing one example of the embodiment of the present invention.

The embodiment of the present invention shall be explained below.

The hair color of the present invention comprises 0.1 to 3% by weight of at least one of water-soluble dyes, 1.5 to 10% by weight of a nonionic or anionic silicone base resin, 0.01 to 1.5% by weight of an amphoteric acryl resin, 3 to 20% by weight of a hair dying auxiliary, 30 to 80% by weight of a lower alcohol and 5 to 50% by weight of water and has a pH controlled to 2 to 5.

The water-soluble dye used in the present invention shall not specifically be restricted as long as it is a water-soluble dye usually used for temporary hair colors and semi-permanent hair colors. An acidic dye is preferably used from the viewpoint of an excellent hair dying property.

To be specific, it can be used in the form of a single compound or a mixture of two or more compounds selected from those prescribed in "Ministerial ordinance prescribing tar colors which can be used for medicines and the like" (notified in 1966, Ministry of Health and Welfare) which do not exert harmful action to human bodies and which are permitted to be used for coloring medicines, quasidrugs and cosmetics.

The specific examples of the acidic dye include Red No. 3 (Erythrosine), Red No. 102 (New Coccine), Red No. 227 (Fast Acid Magenta), Orange No. 205 (Orange II), Yellow No. 4 (Tartrazine), Yellow No. 402 (Polar Yellow 5G), Yellow No. 403 (Naphthol Yellow S), Green No. 3 (Fast Green FCF), Green No. 204 (Pyranine Conc), Blue No. 1 (Brilliant Blue FCF), Blue No. 202 (Patent Blue NA), Purple No. 401 (Alizurol Purple), Brown No. 201 (Resorcin Brown) and Black No. 401 (Naphthol Blue Black), but it shall not be restricted to them.

A content of the above water-soluble dyes has to be 0.1 to 3% by weight (hereinafter referred to merely as "%"), and it is preferably 0.1 to 1%.

If a content of the above water-soluble dyes is less than 0.1%, the hair dying effect is not sufficiently exerted. On the other hand, if it exceeds 3%, the skin and the like are liable to be stained, and therefore both ranges are not preferred.

The nonionic or anionic silicone base resin used in the present invention is added in order to elevate the secondary adhesion and the water resistance.

In the present invention, the nonionic or anionic silicone base resin described above means a block copolymer of a nonionic monomer unit and/or an anionic monomer unit with a polysiloxane unit.

The polysiloxane unit is preferably polydimethylsiloxane.

The anionic monomer includes methacrylic acid, acrylic acid, itaconic acid, maleic acid, fumaric acid and the like, and among them, methacrylic acid and acrylic acid are preferred. The nonionic monomer includes aromatic hydrocarbons such as styrene and (meth)acrylic acid alkyl esters such as methyl methacrylate, ethyl methacrylate, butyl methacrylate, methyl acrylate, ethyl acrylate and butyl acrylate, and among them, esters of methacrylic acid and aliphatic alcohols having 6 or less carbon atoms are preferred, but it shall not be restricted to them.

The silicone base resin described above used in the present invention is particularly preferably a block copolymer of polydimethylsiloxane with methacrylic acid and/or an ester of methacrylic acid and aliphatic alcohol having 6 or less carbon atoms in order to further elevate the secondary adhesion and the water resistance. The block copolymer which is the silicone base resin described above is obtained by a synthetic process in which a polysiloxane compound is allowed to have a polymerization activity at an end and then added a nonionic monomer or an anionic monomer to be polymerized. Usually, a living polymer of polysiloxane compound is produced under the presence of an anionic polymerization initiator, and it is copolymerized with the nonionic monomer or anionic monomer described above, whereby the block copolymer is obtained.

A constitutional proportion of the polysiloxane compound in the block copolymer which is the silicone base resin shall not specifically be restricted, and it is preferably 10 to 80%, more preferably 20 to 70%. If this proportion is less than 10%, the feeling is deteriorated. On the other hand, if it exceeds 80%, a solubility thereof in water and lower alcohols is deteriorated, and therefore both ranges are not preferred.

Further, a number average molecular weight of the block copolymer shall not specifically be restricted, and if the molecular weight is too small, the block copolymer is deteriorated in moisture resistance and colored hair is liable to be discolored by sweat and rain, so that it is preferably controlled to 50,000 or more, preferably 60,000 or more.

A content of the nonionic or anionic silicone base resin described above in the present invention has to be 1.5 to 10% based on the total amount of the hair color in terms of solid, and it is preferably 2 to 5%.

If a content of the above silicone base resin is less than 1.5%, the secondary adhesion and the water resistance are not necessarily satisfactory. On the other hand, if it exceeds 10%, there is caused the defect that the setting power is too strong in finishing after use, and therefore both ranges are not preferred.

The amphoteric acryl resin used in the present invention is added in order to further improve the water resistance and stable reduction in a viscosity of the content liquid.

An N-methacryloyloxyethyl-N,N-dimethylammonium-α-N-methylcarboxybetaine.methacrylic acid alkyl ester copolymer represented by the following Formula (I) is preferably used as the amphoteric acryl resin used in the present invention, and a solution of the copolymer described above in water, ethanol, denatured alcohol or a mixture thereof is preferably used from the viewpoint of the handling property:

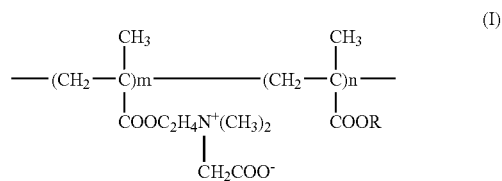

(wherein R is an alkyl group having 1 to 18 carbon atoms, and an average molecular weight of the copolymer is 80,000 to 220,000).

The copolymer represented by Formula (I) described above is a copolymer of N-methacryloyloxyethyl-N,N-dimethylammonium-α-N-methylcarboxybetaine and an alkyl (C1 to C4, C6, C8, C12, C13, C18 and the like) methacrylate.

The amphoteric acryl resin which can specifically be used includes Yukaformer SM (solid content: 30%, average molecular weight: 130,000, 70% solution in ethanol) and Yukaformer 202 (solid content: 30%, average molecular weight: 80,000, 70% solution in ethanol) (all manufactured by Mitsubishi Chemical Corporation) which are commercially available.

A content of the above amphoteric acryl resin in the present invention has to be 0.01 to 1.5% based on the total amount of the hair color in terms of a solid and it is preferably 0.1 to 1.0%.

If a content of the amphoteric acryl resin is less than 0.01%, it becomes impossible to reduce a viscosity of the liquid down to the expected viscosity. On the other hand, if it exceeds 1.5%, the viscosity is suddenly increased, and therefore it is not preferred.

Compounds which are used in conventional acidic hair colors (semi-permanent hair colors) such as benzyl alcohol, phenylethyl alcohol, phenoxyethanol, propylene glycol, N-methylpyrrolidone, gluconic acid lactone, levulinic acid, urea, ethylene carbonate, N-methyl-2-pyrrolidone, α-ketoglutaric acid, γ-butyrolactone, propionamide and acetamide are used alone or in a mixture of two or more kinds thereof as the hair dying auxiliary used in the present invention, and among them, benzyl alcohol and phenylethyl alcohol are preferably used from the viewpoints of the hair dying effect and the stability of the formulated system.

A content of the hair dying auxiliary has to be 3 to 20% based on the total amount of the hair color, and it is preferably 5 to 15%.

If a content of the above hair dying auxiliary is less than 3%, the hair dying effect is not sufficiently exerted. On the other hand, if it exceeds 20%, the drying property is lowered, and therefore both ranges are not preferred.

For example, at least one of ethanol (ethyl alcohol), propanol, butanol, isopropanol and isobutanol is used as the lower alcohol used in the present invention, and ethyl alcohol is preferred in terms of the stability, the drying property and the odor.

A content of the lower alcohol described above has to be 30 to 80% based on the total amount of the hair color, and it is preferably 40 to 70%.

If a content of the above lower alcohol is less than 30%, the drying property is lowered. On the other hand, if it exceeds 80%, the hair dying effect is not sufficiently exerted, and therefore both ranges are not preferred.

For example, refined water, ion-exchanged water, purified water, distilled water and deep ocean water can be used as water used in the present invention, and a content thereof is preferably 5 to 50%, more preferably 10 to 35% based on the total amount of the hair color.

If a content of water is less than 5%, the hair can not sufficiently be swollen, and the hair dying effect is reduced. On the other hand, if it exceeds 50%, the drying property is lowered, and therefore both the ranges are not preferred.

The hair color of the present invention can suitably contain other optional components as long as the effects of the present invention and the stability of the formulated system are not damaged. They include, for example, various surfactants, preservatives, antioxidants, reduction preventives, chelating agents, UV absorbers, viscosity-controlling agents, oil components, silicone derivatives, perfumes, animal and vegetable extracts and publicly known polymer components.

The hair color of the present invention has to be controlled to a pH of 2 to 5, preferably 2 to 4.

If a pH of the hair color is less than 2, the skin is stimulated in a certain case. On the other hand, if the pH exceeds 5, the hair dying effect is reduced, and therefore both the ranges are not preferred.

In the present invention, the pH can be controlled by using organic acids such as formic acid, acetic acid, lactic acid, malic acid, tartaric acid, citric acid and glycolic acid, inorganic acids or salts thereof and, if necessary, alkalis.

A viscosity of the hair color of the present invention is controlled to 8 mPa·s or less, preferably 3 to 6 mPa·s from the viewpoint of easiness in applying on the hair.

If a viscosity of the hair color exceeds 8 mPa·s, the liquid amount adhered to the hair is decreased, and therefore it is not preferred.

When producing the hair color of the present invention, the block copolymer of polydimethylsiloxane with methacrylic acid and/or a methacrylic acid ester as the silicone base resin produces coagulations or deposits due to water falling an acidic area (pH 2 to 5) which is an essential requisite in the present invention, and the resin once coagulated can not be dissolved again by merely adding ethyl alcohol which is a solvent. Accordingly, in producing the hair color of the present invention using the block copolymer of polydimethylsiloxane with methacrylic acid and/or a methacrylic acid ester as the silicone base resin, a vehicle obtained by mixing the block copolymer of polydimethylsiloxane with methacrylic acid and/or a methacrylic acid ester and ethyl alcohol is preferably blended with water and the other components and then homogeneously stirred and mixed.

In order to prevent the block copolymer of polydimethylsiloxane with methacrylic acid and/or a methacrylic acid ester from being deposited to such an extent that the operation is not hindered, a proportion of ethyl alcohol contained in the vehicle described above to water blended is preferably larger than 3:5 in terms of a weight ratio of ethyl alcohol:water.

The blending order of the other blend components constituting the present invention shall not specifically be prescribed, and they may be blended in optional stages.

In using the hair color of the present invention, an applicator for hair is used, and the form and the structure of the applicator for hair used shall not specifically be restricted.

In the present invention, an applicator of a sliver type for hair which is equipped with an applicator main body having a hair color-storing part for storing the hair color in a occlusion body such as a sliver and an applying part provided at a tip part of the above applicator main body and which derives the hair color from the hair color-storing part to the applying part via a deriving member to apply the hair color on the hair is preferably used as the applicator for hair, which can be used from the viewpoints of an applying property on the hair, ability for controlling a liquid amount to be fed into the applying part, less stain caused on cloths, skins and furniture and the usability.

Figure 2:
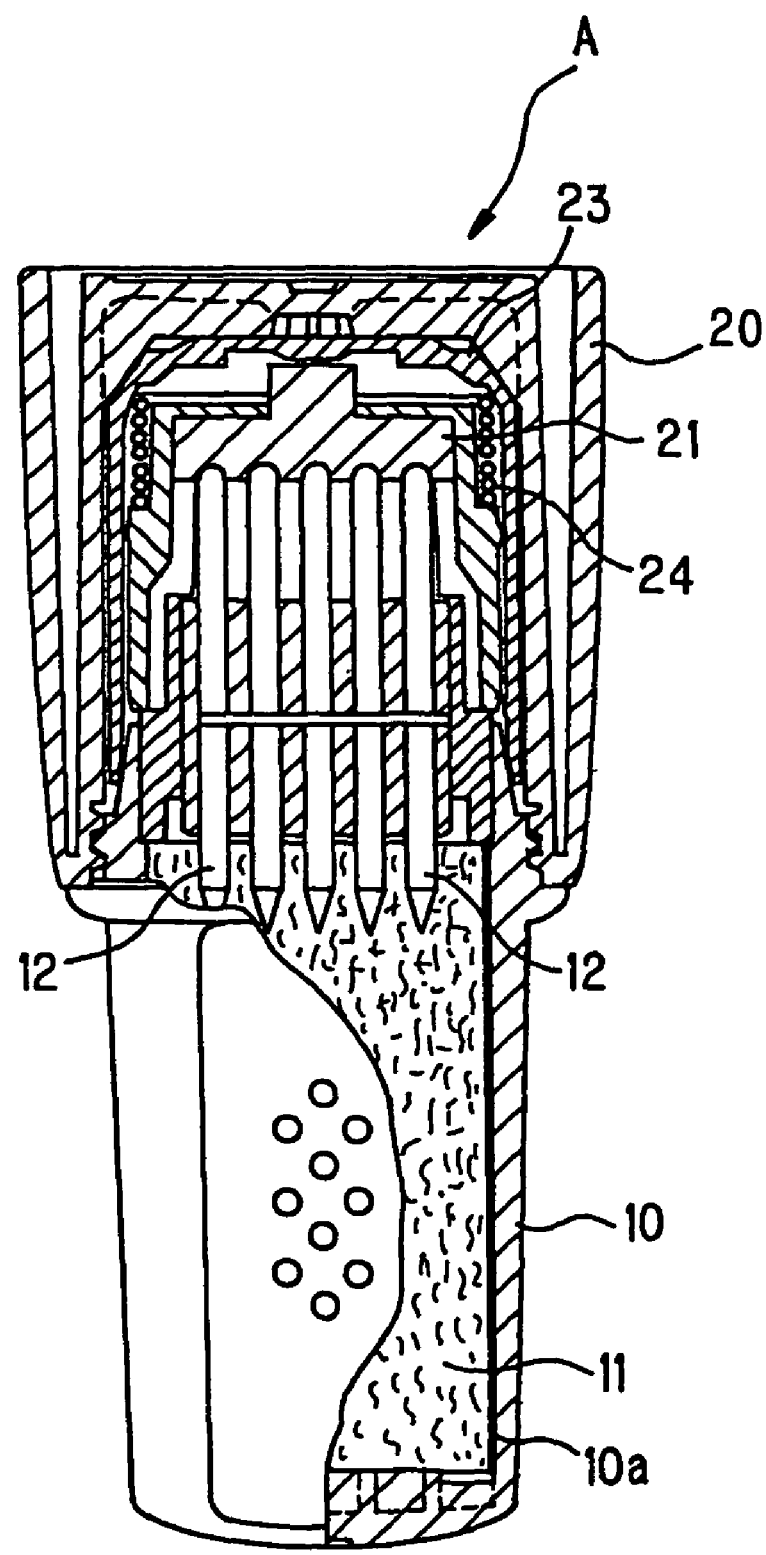
FIG. 2 is a vertical cross-sectional drawing of a side view mode in FIG. 1.
Figure 3:
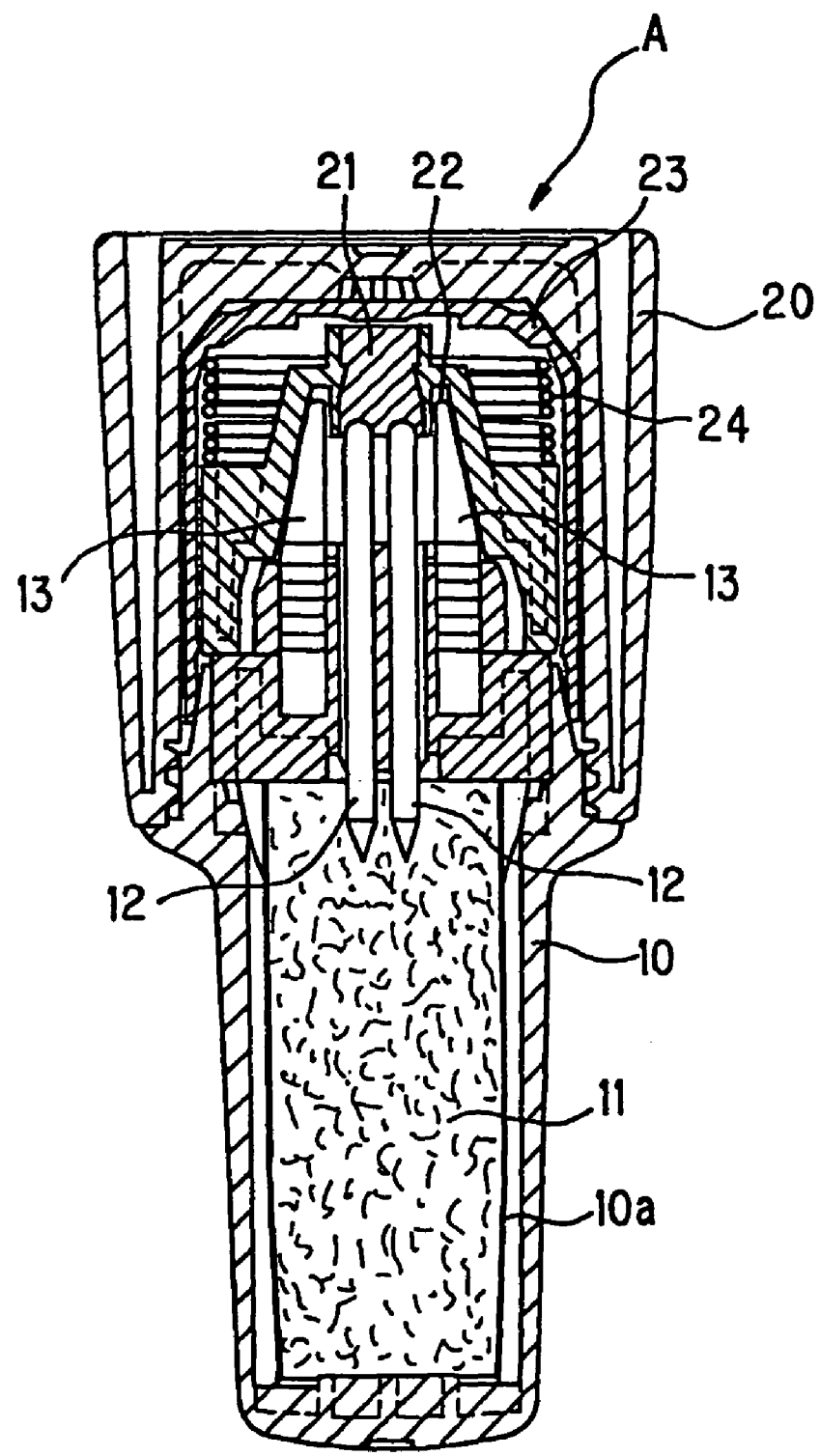
FIG. 3 is a vertical cross-sectional drawing of a front view mode in FIG. 1.

An applicator for hair comprising the above structure is shown in, for example, FIG. 1 to FIG. 3.

An applicator A for hair is given. In this applicator A for hair, a occlusion body 11 occluding a hair color having the constitution described above is, as shown in FIG. 1 to FIG. 3, accomodated in a hair color-storing part 10*a* in the inside of a barrel 10 of an applicator main body; a feed 12 which comprises plural combs for application having capillary action is fixed at a tip part of the barrel 10 in an arrangement of linear lines; the rear part of the feed 12 are connected to the occlusion body 11, and the tip parts of the feed 12 are projected to a front of the barrel 10; comb parts 13 are disposed at a side of the feed 12; a cap member 20 is provided at a tip part of the barrel 10 detachably by screwing; a feed tip-receiving part 21 such as a felt with which the tip parts of the feed 12 are brought into contact is mounted; an inner cap 23 in which a concave part 22 for receiving the tip part of the comb parts 13 is provided at a side of the part 21 is disposed movably in a barrel direction and rotatably in a circumferential direction in the inside of the cap member 20; and the inner cap 23 is urged in an aperture direction of the cap member 20 by a spring member 24.

In the applicator A for hair comprising the above structure, a needed hair color is fed from the occlusion body 11 occluding the hair color described above in the storing part 10*a* to the tip parts of the feed 12 of the applying part, and "blobbing" and unexpected discharge of the liquid are not caused. It can be an applicator for hair which is excellent in carrying and handling properties as well as usability, water resistance and an accumulative hair dying property.

When using the hair color of the present invention by means of the above applicator A for hair, a scalp can be avoided to the utmost from being stained since it has the feed 12 as an applying part, and the hair color can be applied to the hair in the vicinity of the scalp (the borders of the hair). Making sufficiently the best use of the properties of the hair color according to the present invention, the hair color can temporarily be held in the occlusion body, and an optimum amount of the hair color can be applied on the hair via an applying part such as a pen feed.

EXAMPLES

Next, the present invention shall be explained in further details with reference to examples and comparative examples, but the present invention shall not be restricted by the following examples.

Examples 1 to 5 and Comparative Examples 1 to 3

Blend compositions shown in the following Table 1 were homogeneously stirred and mixed by means of a general purpose propeller mixer to obtain the respective hair colors.

Used as a silicone base resin was a block copolymer of methacrylic acid.butyl methacrylate.dimethylpolysiloxane obtained by dissolving azo group-containing polysiloxaneamide (average azo group bonding number: 4.3 groups) having a polysiloxane segment, methacrylic acid and butyl methacrylate (each weight ratio 37:45:18) in ethanol and reacting them at 70 to 80° C. for 10 hours under nitrogen flow.

A mixed vehicle of the silicone base resin of the block copolymer and ethyl alcohol was prepared at first and then the mixed vehicle was blended with water and the other components shown in the following Table 1 and then homogeneously stirred and mixed to obtain hair colors.

The respective hair colors obtained in Examples 1 to 5 and Comparative Examples 1 to 3 described above were measured for a pH and a viscosity by the following methods.

The results thereof are shown in the following Table 1.
Measuring Method of pH

The pH (25° C.) was measured by a conventional method by means of a glass electrode pH meter.
Evaluating Method of Viscosity The respective viscosities at 25° C. were measured by means of an ELD type viscometer (manufactured by Toki Sangyo Co., Ltd.).

Then, an applicator (sliver vessel) for hair having the following structure shown in FIG. 1 to FIG. 3 was filled with 10 ml of the respective hair colors obtained above to evaluate water resistance, a temporary coloring property, an accumulative hair dying property, a drying property after applied, abrasion resistance and an applying property by a silver vessel by the following methods.

The results thereof are shown in the following Table 1.
Structure of Applicator for Hair
Feed: made of PET, intervals of length and breadth between feeds: 3.4 mm, porosity: 80%
Comb parts: made of PBT
Evaluating Method of Water Resistance After the hair color of about 0.1 ml was applied on 2 g of the hair and dried at room temperature for 120 minutes (hereinafter referred to merely as "after applied on the hair and dried"), filter paper wetted with water was pressed thereon to evaluate the degree of the color stuck onto the filter paper according to the following evaluation criteria.
Evaluation Criteria
◎: not stuck at all on filter paper
○: slightly stuck on filter paper
Δ: a little densely stuck on filter paper
X: densely stuck on filter paper
Evaluating Method of Temporary Coloring Property The performance of the hair color as a temporary hair color after applied on the hair and dried was evaluated according to the following evaluation criteria.
Evaluation Criteria
◎: same as commercially available temporary coloring material
○: no problems on practical use
Δ: a little difficult to be dyed
X: not dyed
Evaluating Method of Accumulative Hair Dying Property After applied on the hair and dried, the hair were repeatedly washed three times, and then the accumulative hair dying property was evaluated according to the following evaluation criteria.
Evaluation Criteria
◎: same as commercially available oxidative hair color
○: no problems on practical use
Δ: a little difficult to be dyed
X: not dyed
Evaluating Method of drying Property After Applied The hair color of 0.2 g was applied on 1 g of a bundle of the human hair at 25° C. and 65% RH, and the bundle was touched every 30 seconds with a finger to measure time when the hair color came not to stick on the finger to evaluate the drying property according to the following evaluation criteria.
Evaluation Criteria
◎: within one minute
○: within 3 minutes
Δ: within 5 minutes
X: exceeding 5 minutes
Evaluating Method of Abrasion Resistance The hair color of 0.4 g was applied on 2 g of a bundle of goat hair and dried. This was interposed between two sheets of qualitative filter paper No. 2 manufactured by Advantec Toyo Co., Ltd., and 10 cm of the hair was pulled out in 3 seconds while applying a load of 1 kg. In this case, a density of the color adhered on the filter paper was sensorially evaluated according to the following evaluation criteria.
Evaluation Criteria
◎: densely adhered on the filter paper
○: adhered on the filter paper
Δ: lightly adhered on the filter paper
X: not adhered on the filter paper
Evaluating Method of Applying Property by a Silver Vessel The applying property in applying the hair color by means of an applicator (sliver vessel) for hair was evaluated according to the following evaluation criteria.
Evaluation Criteria
○: a liquid amount adhered on the hair is proper, and the hair color has a good applying property
Δ: a liquid amount adhered on the hair is a little decreased, and the applying property is a little inferior to the case of "good" described above
X: a liquid amount adhered on the hair is decreased, and the applying property is inferior

TABLE 1

(blend unit: % by weight, total amount: 100% by weight)

| | Comparative Example 1 | Example 1 | Example 2 | Example 3 | Comparative Example 2 | Comparative Example 3 | Example 4 | Example 5 |
|---|---|---|---|---|---|---|---|---|
| Water soluble dyes | | | | | | | | |
| Black No. 401 | 0.32 | 0.32 | 0.32 | 0.03 | 0.32 | 0.32 | 0.32 | 0.04 |
| Purple No. 401 | 0.21 | 0.21 | 0.21 | 0.44 | 0.21 | 0.21 | 0.21 | 0.2 |
| Orange No. 205 | 0.33 | 0.33 | 0.33 | 0.43 | 0.33 | 0.33 | 0.33 | 0.5 |
| Red No. 227 | 0.04 | 0.04 | 0.04 | | 0.04 | 0.04 | 0.04 | |
| Yellow No. 403 (1) | | | | | | | | 0.16 |
| Silicone base resin (in terms of solid content)*1 | 3 | 3 | 3 | 2.4 | 3 | 1.2 | 2.4 | 2.4 |
| Amphoteric acryl resin (in terms of solid content)*2 | — | 0.15 | 0.3 | 0.09 | 1.8 | 0.3 | 0.09 | 0.09 |
| Benzyl alcohol | 10 | 10 | 10 | 10 | 10 | 10 | 10 | 10 |
| Glycolic acid | 5 | 5 | 5 | 3.5 | 5 | 5 | 3.5 | 3.5 |
| Refined water | 30 | 30 | 30 | 31.5 | 30 | 30 | 31.5 | 31.5 |
| Ethyl alcohol | 51.1 | 50.95 | 50.8 | 51.61 | 49.3 | 52.6 | 51.61 | 51.61 |
| Viscosity (25° C., mPa·s) | 16.2 | 4.7 | 4.9 | 4.0 | 10.5 | 5.0 | 4.1 | 4.1 |
| pH | 3.0 | 3.1 | 3.2 | 3.3 | 3.8 | 3.4 | 3.3 | 3.3 |
| Water resistance | ○ | ○ | ○ | ○ | ○ | X | ○ | ○ |
| Temporary coloring property | ⊚ | ⊚ | ⊚ | ⊚ | ⊚ | ⊚ | ⊚ | ⊚ |
| Accumulative hair dying property | ⊚ | ⊚ | ○ | ⊚ | Δ | ⊚ | ⊚ | ⊚ |
| Drying property after applied | ○ | ○ | ○ | ○ | Δ | ○ | ○ | ○ |
| Abrasion resistance | ⊚ | ⊚ | ○ | ⊚ | Δ | Δ | Δ | Δ |
| Applying property by a silver vessel | X | ○ | ○ | ○ | X | ○ | ○ | ○ |

*1: methacrylic acid · butyl methacrylate · dimethylpolysiloxane block copolymer
*2: Yukaformer SM (manufactured by Mitsubishi Chemical Corporation)

As apparent from the results summarized in Table 1 shown above, it has been found that the hair colors prepared in Examples 1 to 5 falling in the scope of the present invention are excellent in all aspects of water resistance, a temporary coloring property, an accumulative hair dying property, a drying property after applied, abrasion resistance and an applying property by a silver vessel as compared with those prepared in Comparative Examples 1 to 3 falling outside the scope of the present invention.

In contrast with that, to individually observe the comparative examples, Comparative Example 1 is a case in which the amphoteric acryl resin is not contained, and it has been found that the applying property by a silver vessel is inferior in this case; Comparative Example 2 is a case in which the amphoteric acryl resin is contained in an amount exceeding 1.5%, and it has been found that the finished viscosity is high in this case and that the applying property by a silver vessel is inferior; and Comparative Example 3 is a case in which a content of the silicone base resin is less than 1.5%, and it has been found that the water resistance is inferior in this case.

INDUSTRIAL APPLICABILITY

According to the present invention, provided is a hair color which is excellent in water resistance, an accumulative hair dying property and usability and which is suited to an applicator of a silver type for hair.

The invention claimed is:

1. A hair color for an applicator accommodating an occlusion body comprising 0.1 to 3% by weight of at least one of water-soluble acidic dyes, 1.5 to 10% by weight of a nonionic or anionic silicone base resin which is a block polymer of polydimethylsiloxane and methacrylic acid and/or a methacrylic acid ester, 0.01 to 1.5% by weight of an amphoteric acryl resin which is an N-methacryloyloxyethyl-N,N-dimethylammonium-α-N-methylcarboxybetaine·methacrylic acid alkyl ester copolymer, 3 to 20% by weight of a hair dying auxiliary, 30 to 80% by weight of at least one lower alcohol selected from the group consisting of ethanol, propanol, butanol, isopropanol and isobutanol, and 5 to 50% by weight of water, wherein the hair color has a pH controlled to 2 to 5 and a viscosity of 8 mPa·s or less.

2. The hair color as described in claim 1, wherein the pH of the hair color is controlled by adding a pH controller.

3. The hair color as described in claim 2, wherein the pH controller is selected from the group consisting of organic acids, inorganic acids and salts thereof, and alkalis.

4. The hair color as described in claim 1, wherein the hair color has a viscosity of 3 to 6 mPa·s.

* * * * *